United States Patent
Henneken et al.

(10) Patent No.: US 11,134,917 B2
(45) Date of Patent: Oct. 5, 2021

(54) IMAGING SYSTEM AND METHOD OF DETERMINING A TRANSLATION SPEED OF A CATHETER

(71) Applicant: KONINKLIJKE PHILIPS N.V., Eindhoven (NL)

(72) Inventors: Vincent Adrianus Henneken, Eindhoven (NL); Antonia Cornelia Van Rens, Eindhoven (NL); Roland Wilhelmus Maria Bullens, Best (NL); Arjen Van Der Horst, Eindhoven (NL); Ke Wang, Valkenswaard (NL); Frank Michael Weber, Hamburg (DE); Irina Waechter-Stehle, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 654 days.

(21) Appl. No.: 16/061,352

(22) PCT Filed: Dec. 1, 2016

(86) PCT No.: PCT/EP2016/079364
§ 371 (c)(1),
(2) Date: Jun. 12, 2018

(87) PCT Pub. No.: WO2017/102340
PCT Pub. Date: Jun. 22, 2017

(65) Prior Publication Data
US 2018/0360417 A1    Dec. 20, 2018

(30) Foreign Application Priority Data
Dec. 14, 2015  (EP) .................................... 15199715

(51) Int. Cl.
*A61B 8/00*  (2006.01)
*A61B 5/00*  (2006.01)
(Continued)

(52) U.S. Cl.
CPC .............. *A61B 8/445* (2013.01); *A61B 5/064* (2013.01); *A61B 5/6852* (2013.01); *A61B 8/12* (2013.01);
(Continued)

(58) Field of Classification Search
None
See application file for complete search history.

(56) References Cited

U.S. PATENT DOCUMENTS 4,697,595 A    10/1987  Breyer et al.
4,871,358 A    10/1989  Gold
(Continued)

FOREIGN PATENT DOCUMENTS

WO    2015102573 A1    7/2015

OTHER PUBLICATIONS

Wahle et al "Limitations of the Manual Pullback in Intraconronary Ultrasound Imaging" Proc. of the 20th Annual International Conf. of the IEEE Engineering in Med. and Bio. Soc. vol. 20, No. 1, Oct. 29, 1998 p. 506-509.

*Primary Examiner* — Pascal M Bui Pho
*Assistant Examiner* — Marjan Saboktakin (57) ABSTRACT

Disclosed are an imaging system (10) or an interventional tool, such as a catheter (20), having a first ultrasound transducer array (23) and a second ultrasound transducer array (21) spaced by a fixed distance (D) from each other; wherein both arrays may be used to generate diagnostic images; and a processing arrangement (31, 32) to process a first sensor signal indicative of the first array imaging a reference location (X) at a first point in time, and to process a second sensor signal indicative of the second array imaging the reference location at a second point in time; and determine a translation (pullback) speed of the catheter from the set distance and the difference between the first point in (Continued)

time and the second point in time. Alternatively, a catheter may be provided comprising an ultrasound transducer array at a distal end of the catheter, and two pressure sensors for determining the translation speed.

15 Claims, 6 Drawing Sheets

(51) Int. Cl.
*A61B 8/12* (2006.01)
*A61B 5/06* (2006.01)
*A61B 5/0215* (2006.01)
*A61B 8/08* (2006.01)
*G01S 15/89* (2006.01)

(52) U.S. Cl.
CPC ........ *A61B 8/4461* (2013.01); *G01S 15/8922* (2013.01); *G01S 15/8945* (2013.01); *A61B 5/0215* (2013.01); *A61B 8/085* (2013.01); *G01S 15/8915* (2013.01)

(56) References Cited

U.S. PATENT DOCUMENTS

| | | |
|---|---|---|
| 5,829,439 A | 11/1998 | Yokosawa et al. |
| 5,995,208 A | 11/1999 | Sarge et al. |
| 5,997,479 A | 12/1999 | Savord et al. |
| 6,013,032 A | 1/2000 | Savord |
| 6,241,744 B1 | 6/2001 | Imran et al. |
| 6,275,724 B1 | 8/2001 | Dickinson et al. |
| 6,283,919 B1 | 9/2001 | Roundhill et al. |
| 6,443,896 B1 | 9/2002 | Detmer |
| 6,458,083 B1 | 10/2002 | Jago et al. |
| 6,530,885 B1 | 3/2003 | Entrekin et al. |
| 6,623,432 B2 | 9/2003 | Powers et al. |
| 7,311,714 B1 | 12/2007 | Wscher |
| 7,666,138 B2 | 2/2010 | Ogawa |
| 8,663,110 B2 | 3/2014 | Kim et al. |
| 2003/0114732 A1 | 6/2003 | Webler |
| 2013/0204126 A1 | 8/2013 | Namati et al. |
| 2013/0303914 A1 | 11/2013 | Hiltner et al. |
| 2014/0270436 A1 | 9/2014 | Dascal et al. |
| 2015/0165170 A1 | 6/2015 | Beasley et al. |
| 2015/0182190 A1 | 7/2015 | Hiltner et al. |

FIG. 6 ial Application No.
IMAGING SYSTEM AND METHOD OF DETERMINING A TRANSLATION SPEED OF A CATHETER This application is the U.S. National Phase application under 35 U.S.C. § 371 of International Application No. PCT/EP2016/079364 filed on Dec. 1, 2016, which claims the benefit of EP Application Serial No. 15199715.2, filed Dec. 14, 2015. These applications are hereby incorporated by reference herein.

FIELD OF THE INVENTION

The present invention relates to an imaging system comprising an interventional tool, such as catheter, a sensor arrangement on the interventional tool for generating an in-vivo image and a processing arrangement communicatively coupled to the sensor arrangement.

The present invention further relates to a method of determining a translation speed of the interventional tool, such as catheter, of such an imaging system.

BACKGROUND OF THE INVENTION

Nowadays, catheter-based imaging systems find many applications in application domains where unaided visual inspection may be difficult or impossible, e.g. cavity or drain inspections, and most notably, in medical imaging where such imaging systems may be used to visualize the internals of a patient, for example to detect an anatomical anomaly.

In certain applications, it may be important to be able to accurately determine the size of an object imaged with the imaging system, e.g. in case of the object being a damaged or otherwise anomalous part of the imaged environment, as the size of the imaged anomaly may determine the size of a repair object to be inserted into a channel carrying the anomaly. For example in medical applications, the imaging system may be an intravascular imaging system such as an intravascular ultrasound (IVUS) system used to image a coronary stenosis, in which case the length of the coronary stenosis must be accurately determined in order to determine the appropriate stent to be inserted into the coronary artery to repair the coronary stenosis.

It is not straightforward to determine the size of such an anomaly from the images captured by the imaging system, e.g. due to the lack of (substantial) overlap between subsequently acquired images. Typically, this therefore requires knowledge of the translation, i.e. pull-back, speed of the catheter in order to appropriately scale the imaged anomaly. In order to have a well-defined pull-back speed, the pull-back of the catheter may be motorised. However, in certain application domains such as medical applications, motorised pull-back of the catheter is not preferred because of the overhead in terms of configuration and handling involved with the operation of such an imaging system. This for instance limits the number of investigations that can be performed per unit of time, e.g. per day, which may be undesirable.

US 2013/303914 A1 discloses an intravascular transducer delivery device for use with a patient. The delivery device comprises pressure transducers adapted to measure both a pressure drop across a stenotic lesion and intravascular ultrasound transducers adapted to measure the size of the vessel lumen adjacent the stenotic lesion. The respective sensors are delivered to the site of the stenotic lesion with the same delivery device. This solution is directed to determine the clinical impact of the stenotic lesion in order to determine the appropriate course of action (if any). However, it does not facilitate accurate determination of the size of the stenotic lesion such that where it is decided that the insertion of the stent into the vascular region containing the stenotic lesion is the appropriate course of action, the correct sizing of the stent cannot be derived from the sensor information provided by this delivery device.

SUMMARY OF THE INVENTION

The present invention seeks to provide an imaging system that facilitates accurate determination of the size of an anomaly imaged by the imaging system in a mode of operation employing manual translation (pull-back) of its catheter.

The present invention further seeks to provide a method of determining a translation speed of a catheter of such an imaging system.

According to an aspect, there is provided an imaging system comprising a catheter having a first reference object at a first location on the catheter and a second reference object at a second location on the catheter, the first location and second location being at a set distance from each other; a sensor arrangement including at least one sensor on the catheter for generating an image with the catheter; and a processing arrangement communicatively coupled to the sensor arrangement and adapted to process a first sensor signal from the sensor arrangement indicative of the first reference object in a reference location at a first point in time; process a second sensor signal from the sensor arrangement indicative of the second reference object in the reference location at a second point in time; and determine a translation speed of the catheter from the set distance and the difference between the first point in time and the second point in time.

The provision of multiple reference objects on the catheter at set distances from each other facilitates the determination of the translation speed of the catheter by the sensor arrangement generating respective sensor signals indicative of different reference objects at a particular reference location at different points in time, such that the catheter translation speed can be calculated from the time difference between different reference objects being at the same reference location and the known distance between these reference objects. This facilitates the determination of the size of an anomaly, e.g. an anatomical anomaly, from the images captured by the sensor arrangement, e.g. from a sequence of images imaging the anomaly.

The size of the anomaly may thus be determined by a user of the imaging system. Alternatively, the processor arrangement may be further adapted to determine a size of an anatomical anomaly imaged with the sensor arrangement from the determined translation speed of the catheter; and generate an output indicative of the determined size of said anatomical anomaly. This for instance may be achieved by the processor arrangement being adapted to recognize boundary features of the anomaly in the image is provided by the sensor array, e.g. using well-known image processing algorithms, and translate a time delay between receiving an image containing the first boundary feature and receiving a further image containing a second boundary feature opposite the first boundary feature into a distance between such opposing boundary features using the determined translation speed of the catheter.

In a particularly advantageous embodiment, the at least one sensor comprises an ultrasound transducer arrangement on the catheter for generating an in-vivo ultrasound image, which facilitates in-vivo imaging with minimal health risks for a patient. For example, the imaging system may be an IVUS imaging system.

In another particularly advantageous embodiment, the sensor arrangement comprises a first sensor as the first reference object, the first sensor adapted to provide the processor arrangement with the first sensor signal; and a second sensor as the second reference object, the second sensor adapted to provide the processor arrangement with a second sensor signal, wherein the processor arrangement is adapted to identify the reference location by matching the processed first sensor signal to the processed second sensor signal. In this embodiment, multiple reference sensors are positioned along the catheter at set distances from each other to determine the translation speed of the catheter, which may be sensors dedicated to provide reference data for determining the catheter translation speed or may be sensors having a dual purpose, e.g. to provide imaging data as well as such reference data.

The first sensor may be arranged to generate a first plurality of temporally discrete first sensor signals; the second sensor may be arranged to generate a second plurality of temporally discrete second sensor signals; and the processor arrangement may be arranged to select a second sensor signal from said second plurality for matching to a first sensor signal from said first plurality based on a previously determined translation speed of the catheter. Alternatively, the processor arrangement may be arranged to select a first sensor signal from said first plurality for matching to a second sensor signal from said second plurality based on the previously determined translation speed of the catheter. By predicting which of the sensor signals, e.g. images, in a stream of sensor signals is most likely to match a previously sensor signal received from a downstream sensor, the amount of sensor signal processing required by the processor arrangement may be reduced as not all sensor signals of an upstream sensor need to be processed.

In an embodiment, the first sensor comprises a first ultrasound transducer array and the second sensor comprises a second ultrasound transducer array, and wherein the processor arrangement is adapted to identify the reference location by generating a first ultrasound image generated from the first sensor signal, generating a second ultrasound image generated from the second sensor signal and matching the first ultrasound image to the second ultrasound image. This image matching for instance may be achieved by identification of the same distinct image feature, e.g. the same anatomical landmark, in the first ultrasound image and the second ultrasound image.

It may not be possible to exactly match images from different sensors to each other, for example in scenarios where the orientation or positioning of a downstream sensor relative to the reference location, e.g. a distinct image feature or anatomical landmark, has changed compared to the orientation or positioning of the upstream sensor relative to this reference location. For this reason, the processor arrangement may be adapted to match the first ultrasound image to the second ultrasound image by calculating a correlation between the first ultrasound image and the second ultrasound image; and determining that the first ultrasound image matches the second ultrasound image if the calculated correlation exceeds a threshold value. In other words, where it is determined that such images exhibit the highest (or high enough) degree of similarity, they are considered matching images.

In order to improve the likelihood of finding a match between different images from different sensors, the processor arrangement may be further adapted to perform at least one image adjustment operation on at least one of the first ultrasound image and the second ultrasound image prior to matching the first ultrasound image to the second ultrasound image. Such image adjustment operations for example may be pre-processing operations such as image centering, image intensity normalisation, image rotation correction, and so on.

Alternatively, the first sensor and the second sensor are respective pressure sensors, and wherein the processor arrangement is adapted to identify the reference location by matching a pressure profile obtained from the processed first sensor signal to a pressure profile obtained from the processed second sensor signal. This for instance is particularly advantageous in medical application domains such as intravascular imaging where vascular walls comprising anatomical anomalies typically exhibit pressure profiles characteristic of the anomaly.

In a different embodiment, the sensor arrangement further comprises a sensor external to the catheter adapted to generate the first sensor signal and the second sensor signal, wherein the first reference object is a first marker detectable by the sensor external to the catheter and the second reference object is a second marker detectable by the sensor external to the catheter. Here, the reference location for example may be a reference point of exit of the catheter from a body, e.g. a patient's body, into which the catheter has been inserted. By capturing external sensor signals, e.g. a sequence of images of part of the catheter, in this reference location, the appearance of respective reference objects a different point in time in these external sensor signals is used to derive the translation (pull-back) speed of the catheter from the body.

According to another aspect, there is provided a method of determining a translation speed of a catheter of an imaging system, the catheter comprising a first reference object at a first location on the catheter and a second reference object at a second location on the catheter, the first location and second location being at a set distance from each other, the image system further comprising a sensor arrangement including at least one sensor on the catheter for generating an image with the catheter, the method comprising processing a first sensor signal from the sensor arrangement indicative of the first reference object in a reference location at a first point in time; processing a second sensor signal from the sensor arrangement indicative of the second reference object in the reference location at a second point in time; and determining the translation speed of the catheter from the set distance and the difference between the first point in time and the second point in time.

This provides an accurate determination of the translation speed of the catheter even in scenarios where the catheter is manually refracted (pulled back) from the body into which the catheter has been inserted. This for instance facilitates the calculation of the size of anomaly such as an anatomical anomaly within a portion of the body imaged by the sensor arrangement on the catheter.

In an embodiment, the method further comprises generating a sequence of images indicative of the size of an anatomical anomaly with the sensor arrangement over a period of time; calculating the size of the anatomical anomaly from the period of time and the determined translation speed of the catheter; and generating an indication of the calculated size of the anatomical anomaly. Such automatic calculation of the size of the anatomical anomaly yields a particularly efficient operation of the imaging system, thus minimizing the time required to determine the size of the anatomical anomaly and maximising patient throughput on the imaging system.

In an embodiment, the first sensor signal is a first image signal and the second sensor signal is a second image signal, the method further comprising generating a first image generated from the first sensor signal; generating a second image generated from the second sensor signal; and matching the first image to the second image, for example by identification (and superposition) of a distinct image feature in both images.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

It should be understood that the Figures are merely schematic and are not drawn to scale. It should also be understood that the same reference numerals are used throughout the Figures to indicate the same or similar parts.

The embodiments of the present invention are applicable to any type of imaging system including a catheter for investigating a confined space. In particular advantageous embodiments, the imaging system is a medical imaging system, such as an ultrasound diagnostic system. A particularly advantageous example of such an ultrasound diagnostic system is an intravascular ultrasound (IVUS) imaging system. In the remainder, embodiments of the imaging system will be described using an IVUS imaging system by way of non-limiting example only, as it should be understood that the described imaging system may be adapted for different application domains without requiring inventive skill by a person skilled in the art.

IVUS imaging procedures are widely used in interventional cardiology as a diagnostic tool for assessing a vessel, such as an artery, within the body of the patient to determine the need for treatment, to guide intervention, and/or to assess the effectiveness of administered treatment. An IVUS imaging system uses ultrasound echoes to form a cross-sectional image of the vessel of interest. Typically, IVUS imaging uses a transducer in a catheter to emit ultrasound signals (waves) and to receive the reflected ultrasound signals. The emitted ultrasound signals (often referred to as ultrasound pulses) pass easily through most tissues and blood, but they are partially reflected by discontinuities arising from tissue structures (such as the various layers of the vessel wall), red blood cells, and other features of interest, e.g. a coronary stenosis.

Figure 1:
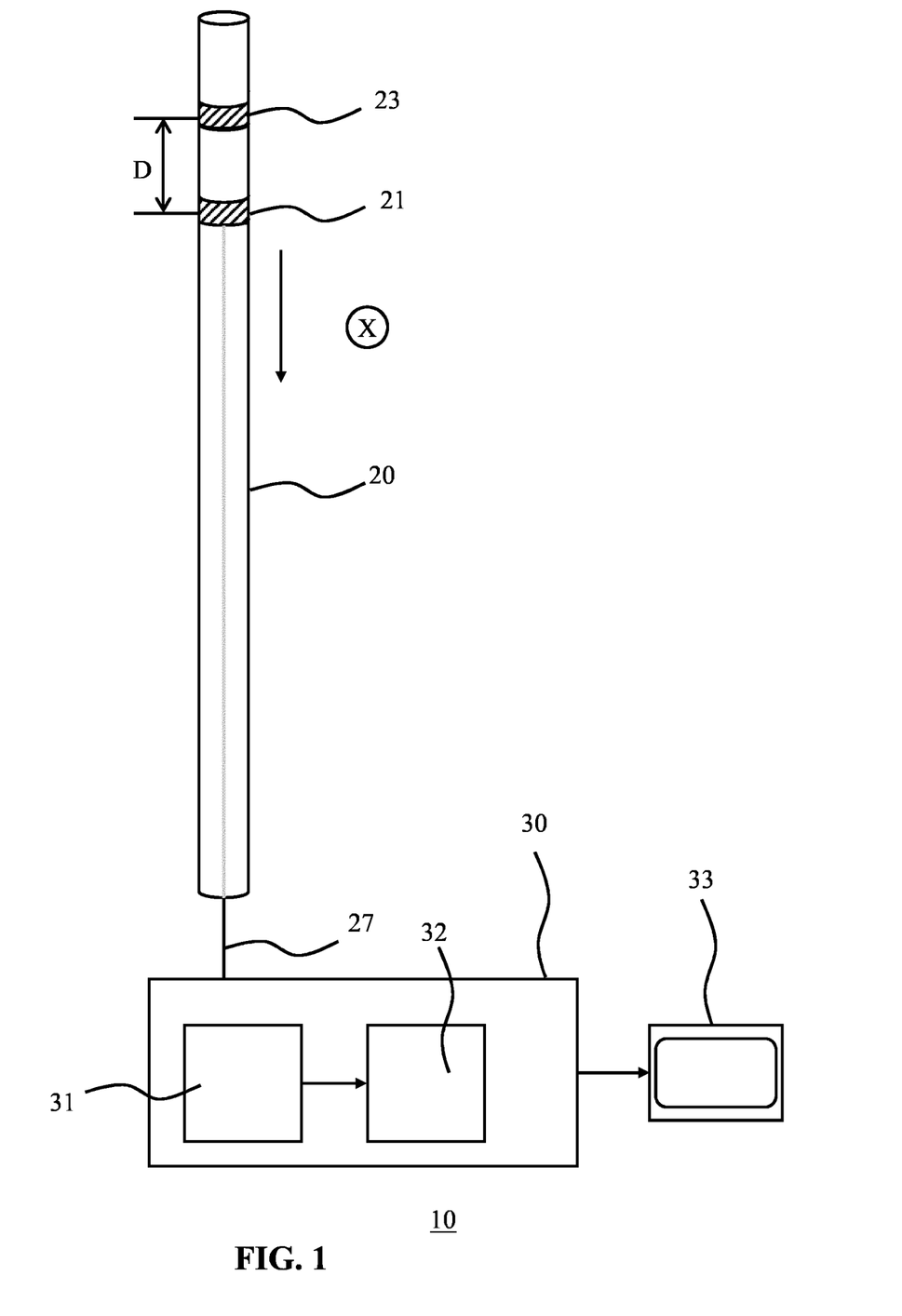
FIG. 1 schematically depicts an imaging system according to an embodiment.

FIG. 1 schematically depicts an IVUS imaging system 10 including a catheter 20 communicatively connected to a patient interface module 30 through a communication structure 27, e.g. one or more conductive wires, which may form part of a larger structure such as a coaxial cable. The catheter 20 may be any suitable catheter, such as a solid-state catheter or a rotational catheter. An embodiment including a solid-state catheter will now be described in more detail by way of non-limiting example only.

The catheter 20 comprises an array 23 of transducers, here distributed around a circumference of a sheath, which is an outer layer of the catheter 20, e.g. near a distal end of the catheter 20 although it should be understood that the array 23 of transducers may be positioned in any suitable location, e.g. at the distal end of the catheter 20. The array 23 of transducers may be formed in any suitable manner, e.g. by providing a plurality of transducer chips on a flexible carrier to facilitate the wrap-around of the array 23 around the sheath of the catheter 20. Each chip may comprise one or more ultrasound transducers. Any suitable type of ultrasound transducers may be used for this purpose, e.g. piezoelectric transducers, e.g. transducers formed of piezoelectric materials such as PZT and PVDF, or capacitive micromachined ultrasound transducers (CMUT) in which a cavity separates opposing electrodes, with a bottom electrode supported on a substrate of the CMUT cell and a top electrode supported by a flexible membrane, as is well-known per se. CMUT elements are particularly preferred due to their lower cost and improved impedance characteristics compared to piezoelectric transducers.

The transducers are connected to an electronic multiplexer circuit (not shown), which may be located in the patient interface module 30, which typically comprises circuitry including one or more processing units, which will also be referred to as a processing arrangement. The multiplexer circuit may form part of the processing arrangement or may be a separate circuit in the patient interface module 30. Alternatively, at least part of the multiplexer circuit may be realized in circuitry embedded within the catheter 20. The multiplexer circuit is typically adapted to (sequentially) select transducers from the array 23 for transmitting ultrasound signals and receiving reflected ultrasound signals. By stepping through a sequence of transmit-receive transducer pairs, the solid-state catheter 20 can be used to synthesize the effect of a mechanically scanned transducer element, but without moving parts. Since there is no rotating mechanical element, the transducer array 23 can be placed in direct contact with blood and vessel tissue with minimal risk of vessel trauma.

The catheter 20 may comprise one or more lumens through which additional structures, e.g. a guide wire, may be fed as is well-known in the art. The catheter sheath may be made of any flexible material, e.g. any suitable flexible polymer. Such materials are well-known per se and are therefore not further elaborated upon for the sake of brevity only.

The catheter 20 further comprises a further array of transducers 21 at a fixed distance D from the array of transducers 23. The further array of transducers 21 preferably is identical to the array of transducers 23 such that both transducer arrays can generate substantially identical images when located in substantially the same location, e.g., substantially the same location relative to a reference point X when in use. In the case of a medical imaging system 10, such a reference point X for example may be a distinct image feature such as an anatomical landmark within the part of the patient's body that is being imaged. Such a distinct image feature may be selected by a user of the imaging system 10, e.g. using a user interface (not shown) of the patient interface module 30, e.g. by selecting the distinct image feature in an image displayed on the display device 33. Alternatively, such a distinct image feature may be automatically selected by the processing arrangement, e.g. using one or more suitable feature recognition algorithms.

The further array 21 of transducers may act as a first sensor imaging a reference point X at a point in time T1 during translation, i.e. pullback of the catheter 20 from a body, e.g. a patient's body, being imaged with the imaging system 10. Such a first sensor may also be referred to as a downstream sensor. The array 23 of transducers may act as a second sensor imaging the reference point X at a point in time T2 during such translation of the catheter 20, with the array 23 producing substantially the same image of the reference point X as the array 21, but after a certain time delay $\Delta T=T2-T1$. Such a second sensor may also be referred to as an upstream sensor. Consequently, the translation speed S of the catheter 20 may be calculated as $S=D/\Delta T$.

To this end, the processing arrangement of the patient monitoring unit 30 comprises a signal processor 31 communicatively coupled to the array 23 and the further array 21, which signal processor 31 is adapted to process the echo signals received from the respective arrays. The signal processor 22 may process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and microbubbles. The signal processor 31 optionally may perform additional signal enhancement such as speckle reduction, signal compounding, and noise elimination. The bandpass filter in the signal processor 31 may be a tracking filter, with its passband sliding from a higher frequency band to a lower frequency band as echo signals are received from increasing depths, thereby rejecting the noise at higher frequencies from greater depths where these frequencies are devoid of anatomical information. Such signal processing techniques are well-known per se and are therefore not explained in further detail for the sake of brevity only. Furthermore, it should be understood that additional signal processing techniques that are well-known per se to the person skilled in the art may be employed by the signal processor 31.

The signal processor 31 may further operate as an image processor or may provide the processed echo signals to a separate image processor 32 forming part of the processing arrangement of the patient monitoring device 30. The image processor 32 is typically configured to determine if a first image produced from the echo signals of the first sensor, i.e. further transducer array 21, matches a second image produced from the echo signals of the second sensor, i.e. transducer array 23. To this end, the image processor 32 may employ an algorithm using a metric based on maximizing image correlation. For example, a correlation function may use an image correlation C, which may be defined as:

$$C = \frac{\sum I_{a,i} I_{b,i}}{\sum I_{a,i}^2 \sum I_{b,i}^2}$$

In this equation, $I_{a,i}$ and $I_{b,i}$ are the intensities of the first image and the second image respectively. In order to calculate the correlation between the first and second image, the image processor 32 may be further adapted to apply suitable image pre-processing steps prior to calculating the correlation between these images. For example, the image processor 32 may employ image centering algorithms and/or image intensity normalization algorithms in order to improve the accuracy of the correlation calculation. In addition, the image processor 32 may detect that the second image is rotated relative to the first image, e.g. due to a rotation of the catheter 20 during its translation, e.g. pullback. In such a scenario, the image processor 32 may be adapted to compensate for such inter-image rotation. For example, suitable image rotation compensation algorithms include determination of I(phi) by integration along the image radius, the use of 1-D correlation algorithms to find the most likely angular offset, iteration estimation algorithms of image position an angle, and so on. Such techniques are well-known per se and are therefore not explained in further detail for the sake of brevity only. Furthermore, it should be understood that additional signal processing techniques that are well-known per se to the person skilled in the art may be employed by the image processor 32. The image processor 32 may apply a correlation threshold to determine if the first image matches the second image, i.e. may decide that such a match exists if image correlation C exceeds a set threshold value. To further improve the image matching process, the first image may be compared to a series of second images, e.g. consecutively captured second images, with the second image having the largest (maximum) correlation with the first image being selected as the matching image, if its image correlation C also exceeds the threshold value. This is for example preferable in scenarios where it is likely that multiple second images may 'match' the first image in terms of having an image correlation C exceeding the set threshold value, in which case the second image having the best match, i.e. the maximum correlation, with the first image may be selected to increase the accuracy of the determination of the translation speed of the catheter 20.

In order to determine the time delay or difference $\Delta T$ between matching images, the processing arrangement of the patient interface module 30, e.g. the signal processor 31 or the image processor 32, may employ a clock that provides each generated image with a timestamp. Alternatively, a separate clock may be used for this purpose. As such timestamping techniques are well-known per se, they will not be explained in further detail for the sake of brevity only.

The image processor 32 may be adapted to, upon determination of a reference location, e.g. an anatomical landmark, in an image produced by a downstream sensor, to evaluate every subsequent image produced by an upstream sensor until the best matching image produced by the upstream sensor has been identified. However, where the respective transducer arrays produce images at high rates, it may be desirable to reduce the computational effort required by the image processor 32 in order to match these respective images. In an embodiment, the image processor 32 is adapted to evaluate a subset of the images only produced by the upstream sensor, i.e. the transducer array 23, which subset is selected based on a previously determined translation speed of the catheter 20. For example, the image processor 32 may be adapted to only evaluate images produced by the upstream sensor within a certain time window $W=[T_a, T_b]$, with $Ta=S*D*A$ and $Tb=S*D*B$, with A and B scaling factors with $A<1$ and $B>1$, e.g. $0.5 \le A<1$ and $1<B \le 1.5$, such that a reduction or an increase in translation speed of the catheter 20 up to 50% is factored into the evaluation. Other suitable values of the scaling factors A and B will be immediately apparent to the skilled person. It will be apparent to the skilled person that analogously the image processor 32 may be adapted to evaluate a subset of images produced by the downstream sensor within a certain time window to find the best match with an image produced by the upstream sensor.

In an embodiment, the processing arrangement of the patient interface module 30, e.g. the image processor 32, may be adapted to calculate the translation speed of the catheter 20, e.g. its pullback speed, from a complete sequence of images captured with the respective transducer arrays 21, 23, which may be performed during or after acquisition of these images. In this embodiment, the processing arrangement may be adapted to apply regularization techniques such as a Kalman filter to the image sequence in order to obtain a particularly accurate determination of the translation speed of the catheter 20.

Both the transducer array 23 and the further transducer array 21 may be used to generate diagnostic images, e.g. a composite image in which a first portion of the image is generated by the transducer array 23 and a second portion of the images generated by the further transducer array 21. In the context of the present application, a diagnostic image may be an image used for a medical diagnosis of a particular condition within the body of a patient or may be an image for diagnosing a problem in a non-medical application domain as previously explained. Alternatively, one of the transducer arrays may solely be used for the purpose of determining the translation speed of the catheter 20.

Figure 2:
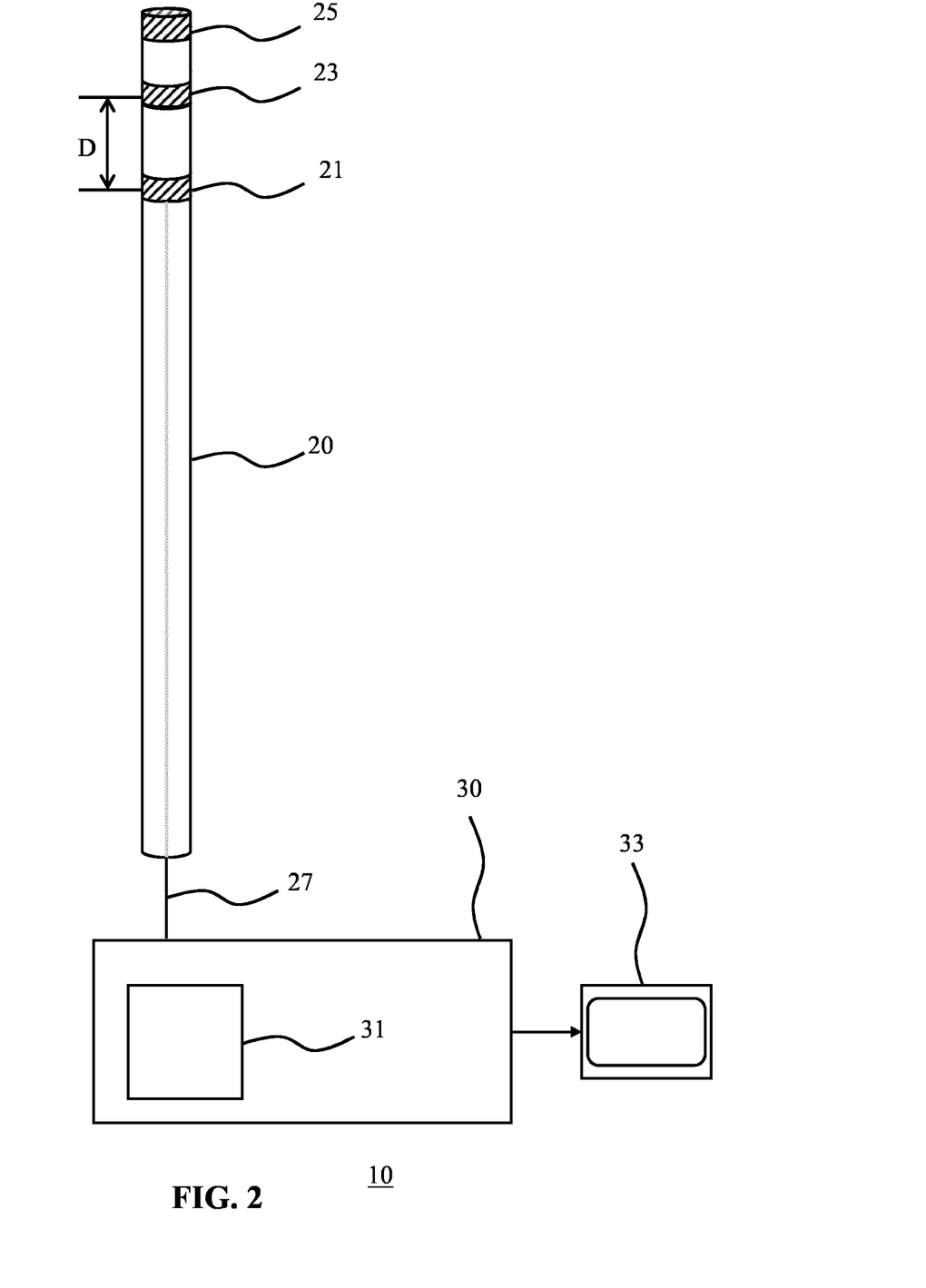
FIG. 2 schematically depicts an imaging system according to another embodiment.

At this point, it is noted that the determination of the translation speed of the catheter 20 is not limited to a transducer array 21 displaced on the catheter 20 by a distance D relative to a transducer array 23 on the catheter 20. Any type of sensor that is capable of generating a sensor signal from which a reference point such as a distinct image feature or anatomical landmark can be recognized may be used for this purpose. For example, FIG. 2 schematically depicts an embodiment of the imaging system 10 in which the catheter 20 comprises an ultrasound transducer array 25 at a distal end of the catheter 20, with the catheter 20 further comprising a first pressure sensor 21 at a set distance D from a second pressure sensor 23 on the catheter 20. It is noted for the avoidance of doubt that the location of the first pressure sensor 21, second pressure sensor 23 and ultrasound transducer array 25 on the catheter 20 as shown in FIG. 2 is by way of non-limiting examples only and that any suitable location for any of the sensors may be contemplated, e.g. a location of the ultrasound transducer array 25 in between the first and second pressure sensors or upstream from the first and second pressure sensors, i.e. closest to the proximal end portion of the catheter 20. Capacitive MEMS pressure sensors are particularly preferred as this facilitates both CMUT image sensors and the MEMS pressure sensors to be manufactured in the same manufacturing process. However, it should be understood that other suitable type of pressure sensors, e.g. (piezo-resistive) strain gauges or Fabry-Perot pressure sensors, may be alternatively deployed.

In this embodiment, at least one of the first pressure sensor 21 and the second pressure sensor 23 may be included in the catheter 20 to provide further diagnostic information to be processed by the processing arrangement of the patient interface module 30, e.g. to obtain pressure information from the wall of the blood vessel, e.g. an artery or vein, as is well-known per se. In an embodiment, both the first pressure sensor 21 and the second pressure sensor 23 are included in the catheter design to provide such diagnostic information. Such pressure sensors typically generate pressure profile information, with the pressure profiles may be compared with each other in analogy to the above described image comparison in order to match a first pressure profile generated by the first pressure sensor 21 to a second pressure profile generated by the second pressure sensor 23 after a time delay $\Delta T$, such that the translation speed, e.g. the pullback speed, of the catheter 20, may be calculated from the known distance D between the first pressure sensor 21 and the second pressure sensor 23 and the determined time delay $\Delta T$.

In the above embodiments, the imaging system 10 comprises a pair of sensors on the catheter 20 for capturing sensor data from which a landmark such as an anatomical landmark can be distinguished, e.g. distinct image features or pressure profiles. Such sensors may form part of the overall imaging functionality of the imaging system 10 or may be sensors dedicated to the determination of the translation speed of the catheter 20 as previously explained.

Figure 3:
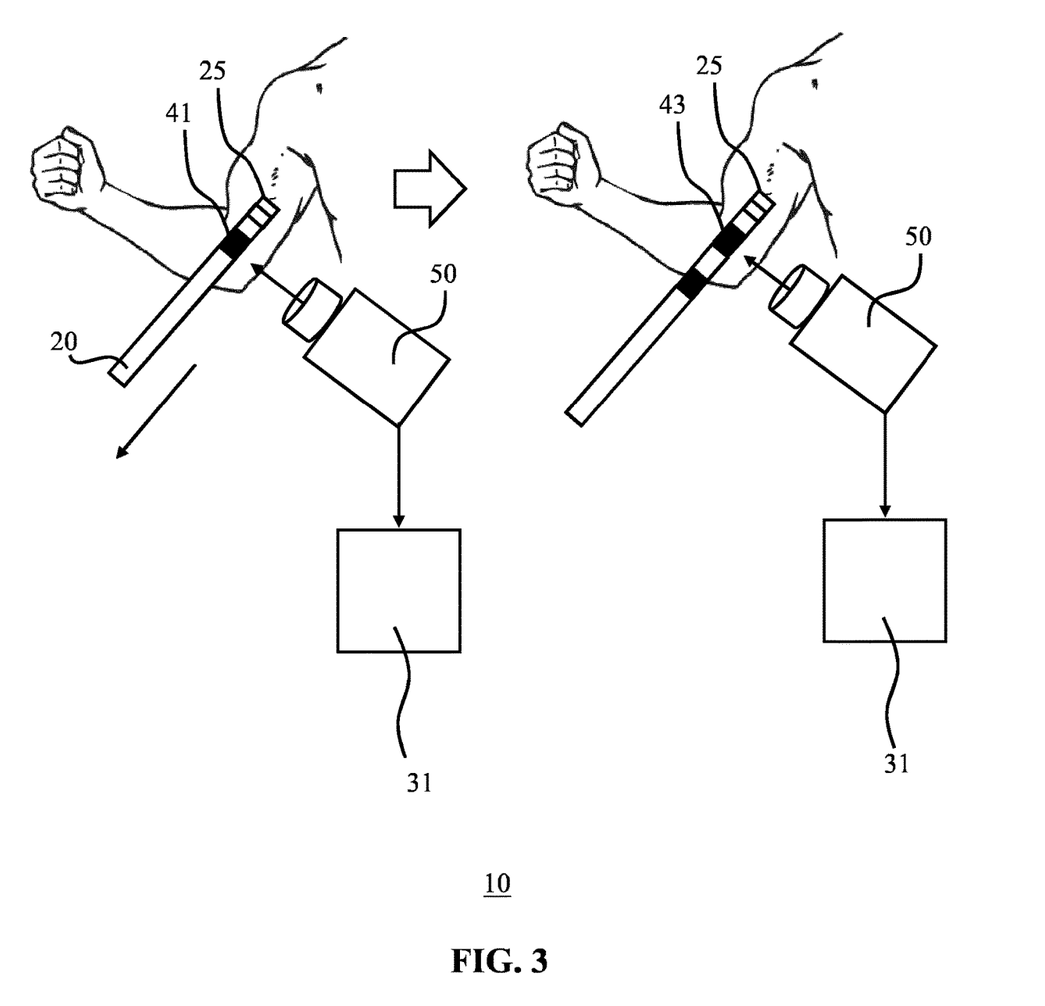
FIG. 3 schematically depicts an imaging system according to yet another embodiment.

FIG. 3 schematically depicts an alternative embodiment in which the sensor arrangement of the imaging system 10 comprises an external sensor 50 in addition to one or more sensors on the catheter 20. In this embodiment, next to the sensor 25 for generating an image with the catheter 20 the catheter 20 comprises a first marker 41 detectable by the external sensor 50 and a second marker 43 detectable by the external sensor 50 at a set distance D from the first marker 41. For example, the external sensor 50 may be an image sensor, which may be integrated in an imaging device such as a camera. In this embodiment, the first marker 41 and the second marker 43 may be visual markers that can be recognized in images captured by the image sensor. Alternatively, the first marker 41 and the second marker 43 may be inductive or magnetic markers detectable by an inductive or magnetic external sensor 50 respectively. Other suitable detection principles may be contemplated.

During operation, the external sensor 50 is typically positioned within sensor range of the catheter 20. For example, in the case of the external sensor 50 being an image sensor, the image sensor is typically positioned such that an image of the catheter 20 as it is being pulled back from a body (here symbolized by a human arm by way of non-limiting example only) is captured by the image sensor such that the appearance of such a visual marker emanating from the body being imaged can be captured. In this embodiment, the body orifice through which the catheter 20 is inserted into the body (or a fixed location in the vicinity of this body orifice) may be used as the reference location used to determine the translation speed of the catheter 20, with the image sensor typically set up to capture a sequence of images, e.g. at set intervals, of the reference location such that an appearance of one of the visual markers in this reference location is captured in one of the images captured by the image sensor. As will be readily understood by the skilled person, the same operating principle may be applied to different types of external sensors 50, e.g. magnetic or inductive sensors as previously explained. The time interval $\Delta T$ between the appearance of the first marker 41 in the reference location (as shown in the left pane) and the appearance of the second marker 43 in the reference location (as shown in the right pane) may be determined by identification of the respective markers in the sensor signals provided by the external sensor 50.

To this end, the external sensor 50 may be communicatively coupled to the processing arrangement of the patient interface module 30, e.g. to the signal processor 31 and/or to the image processor 32, with the processing arrangement adapted to analyze the sensor data provided by the external sensor 50 (e.g. images in case of an image sensor), e.g. using feature recognition algorithms, which algorithms are well-known per se and are therefore not described in further detail for the sake of brevity only, in order to identify a first sensor signal (e.g. image) identifying the first marker 41 and a second sensor signal identifying the second marker 43. The external sensor 50 may assign a timestamp to each sensor signal sent to the patient interface module 30 or alternatively the processing arrangement may assign such a timestamp to each sensor signal received from the external sensor 50 as previously explained. The time delay ΔT may subsequently be calculated from the difference in the respective timestamps of the sensor signals comprising the first marker 41 and the second marker 43 respectively in the reference location.

In case of the first marker 41 and the second marker 43 being visual markers, any suitable visual marker may be used as the first visual marker 41 and the second visual marker 43. Preferably but not necessarily, the first visual marker 41 and the second visual marker 43 are identical markers, as this facilitates easy recognition of these markers in the images provided by the image sensor 50. The visual markers may be an integral part of the catheter 20 or may be attached thereto, e.g. as an adhesive tape or the like. The visual markers may have a contrasting colour to the colour of the catheter 20 to facilitate their recognition and/or may be a surface disruption such as an indentation or a ridge on the outer surface of the catheter 20, e.g. on its sheath. In case of a medical imaging system 10, the visual markers are biocompatible visual markers, i.e. visual markers that may be inserted into a patient's body without undue risk to the health and safety of the patient.

The principle of the embodiment depicted in FIG. 3 can be also implemented for an interventional tool tracking, such as catheter, with or without the sensor for generating an image. The sensor arrangement of the imaging system may be used for tracking the translation speed of the interventional tool advancing in the body by means of the external sensor 50 via processing the first sensor signal from the sensor arrangement indicative of the first reference object, such as marker 41, at the first location and the second reference object, such as marker 43, at the second location.

It shall be understood that the principle of the present invention is applicable not only to the catheters but to a broader class of interventional tools. In an aspect of the present invention the interventional tool comprises the first reference object 21, 41 at a first location on the tool and the second reference object 23, 43 at a second location on the tool, the first location and second location being at a set distance D from each other; a sensor arrangement 21, 23, 25, 50 communicatively connectable to a processing arrangement 31, 32 and comprising at least one sensor on the catheter for generating an image with said tool, wherein when the interventional tool is being translated with a given translation speed the sensor arrangement is arranged to provide to the processing arrangement 31, 32 a first sensor signal indicative of the first reference object in a reference location X at a first point in time and a second sensor signal indicative of the second reference object in the reference location at a second point in time.

Yet another aspect of the present invention relates to the processing arrangement communicatively connectable to the sensor arrangement from the interventional tool and adapted to process the first sensor signal indicative of the first reference object in the reference location at the first point in time; process the second sensor signal indicative of the second reference object in the reference location at the second point in time; and determine the translation speed of the tool from the set distance and the difference between the first point in time and the second point in time.

The established means of the communicative connection between the interventional tool 20 and the processing arrangement 31, 32 may be one of wire-based and wireless.

In another aspect of the present invention a software implemented algorithms is provided, said algorithm enabling a computer processor to perform functions of the processing arrangement 31,32 such as process the first sensor signal from the sensor arrangement indicative; processing the second sensor signal from the sensor arrangement; and determining the translation speed of the interventional tool, such as catheter, from the set distance and the difference between the first point in time and the second point in time.

Figure 4:
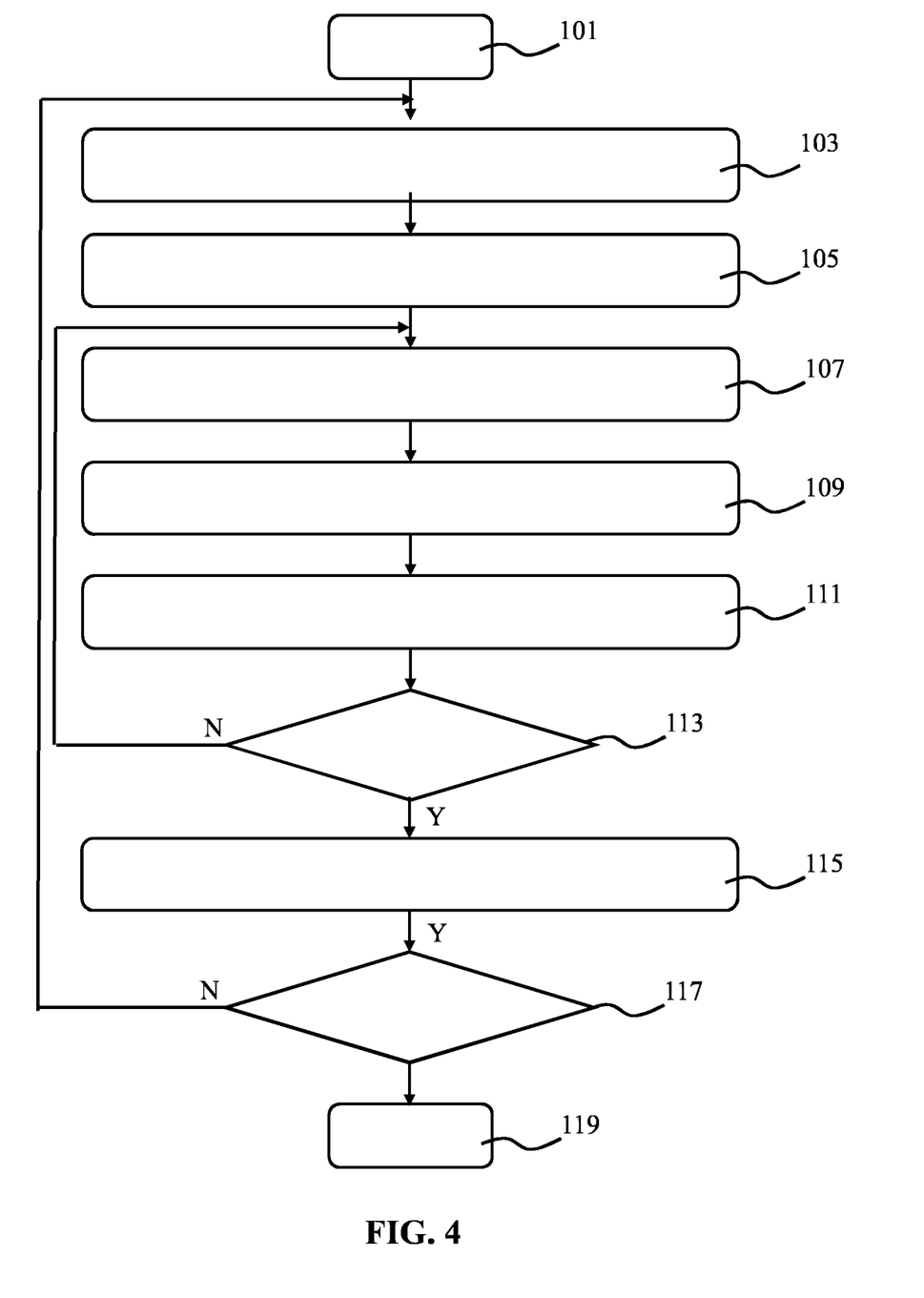
FIG. 4 schematically depicts a flowchart of a method of determining a catheter pull-back speed according to an embodiment.

FIG. 4 schematically depicts a method to determine the translation speed of a catheter 20 using the imaging system 10 according to embodiments of the present invention. It shall be also understood that the described below method can be used for a non-medical application such as cavity or drain inspections, wherein precise measurements of the inspected cavity by a translatable tool (instead of the catheter compared to the medical application) may be required. The method starts in 101, e.g. with the insertion of the catheter 20 into a body, e.g. a patient's body, the imaging of the internals of the body, and the initiation of the pull-back of the catheter 20. In 103, first sensor data relating to a first reference point on the catheter 20 being in the reference location is captured. As previously explained, this may be sensor data generated by a first sensor on the catheter 20, which sensor data includes a distinct image feature, e.g. a landmark such as an anatomical landmark, or may be sensor data provided by an external sensor capturing a first detectable marker appearing from the body. In 105, the sensor data indicative of this reference location is processed by the processing arrangement of the imaging system 10, e.g. to identify the (anatomical) landmark or the detectable marker and to identify or assign a timestamp to the sensor data.

In 107, second sensor data relating to a second reference point on the catheter 20 being in the reference location is captured, e.g. sensor data generated by a second sensor on the catheter 20, which sensor data also includes the distinct image feature such as an (anatomical) landmark, or may be sensor data provided by an external sensor capturing a second detectable marker appearing from the body. The second sensor data subsequently is processed in 109, which processing may include pre-processing steps, such as for example in the case of the first and second sensor data relating to ultrasound images, where image preprocessing may be performed as explained above in order to facilitate the determination of the correlation between these images.

In 111, the processed data is compared with each other to see if the data is matching, that is, if both the first sensor data and the second sensor data correlated to each other in the sense that both comprise a (pre-)defined distinct image feature such as a landmark or a detectable marker in a defined location. If it is determined in 113 that no such correlation exists, the second sensor data does not match the first sensor data and the method reverts back to 107 in which new second sensor data is captured. This is repeated until it is determined in 113 that the first sensor data matches the second sensor data, after which the translation speed, e.g. the pullback speed, of the catheter 20 is determined in 115 from the known distance D between the first sensor 21 and the second sensor 23 (or the first visual marker 41 and the second visual marker 43) and the time difference ΔT between the time of capture of the first sensor signals and the time of capture of the second sensor signals as previously explained. It is reiterated that where reference is made to the first sensor data matching the second sensor data in step 113, this is intended to include finding the second image that has the largest image correlation C with the first image. There may be more than one second image that matches the first image in the sense that each of such second images exhibit an image correlation C with the first image above a defined threshold (or vice versa), in which scenario the second image having the highest image correlation C may be selected as the matching image.

It is determined in 117 that the determination of the translation speed of the catheter 20 has been completed, the method terminates in 119, else the method may revert back to 103 to perform another determination of the translation speed.

Figure 5:
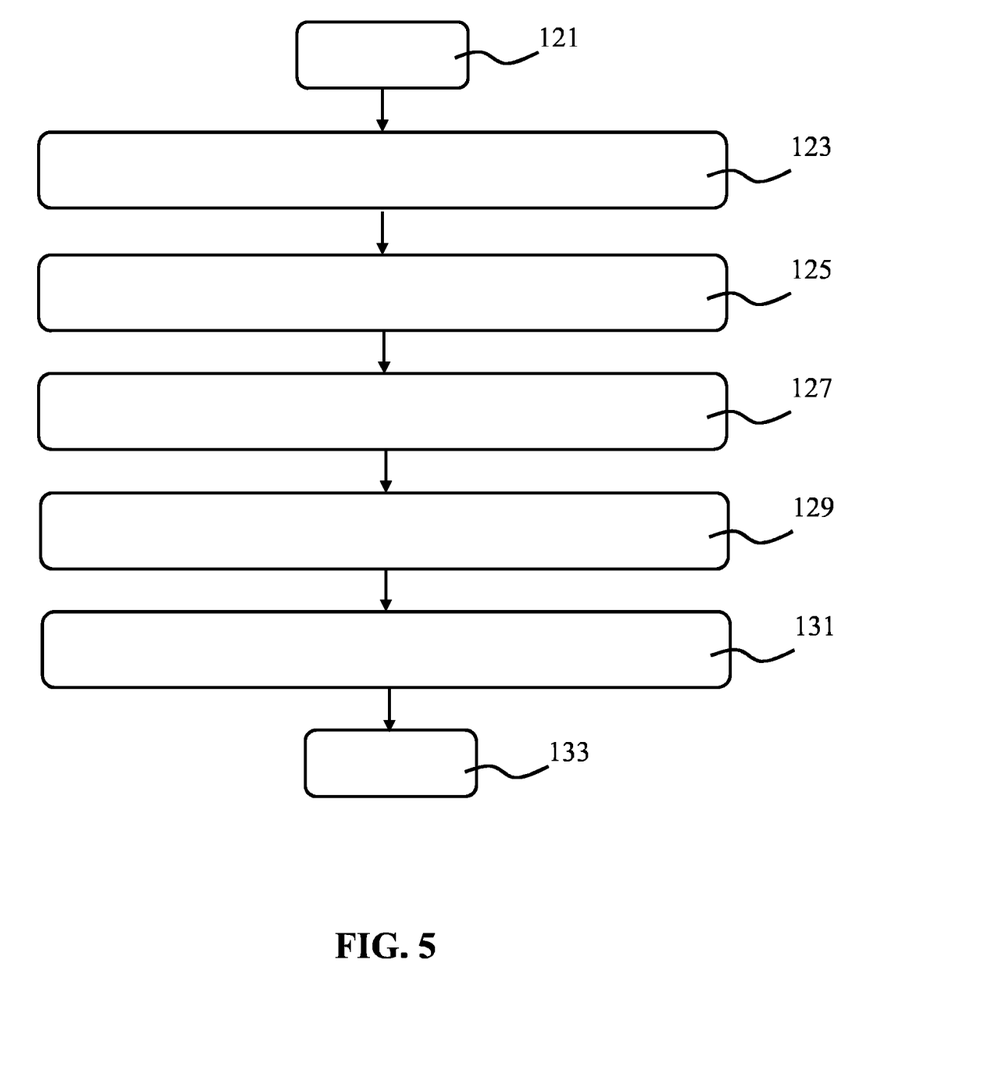
FIG. 5 schematically depicts a flowchart of a method of determining an anomaly size according to an embodiment.

FIG. 5 is a flow chart of a method of determining the size of an anomaly imaged by the imaging system 10 using the catheter translation speed as determined with the method of FIG. 4. The method starts in 121 with the insertion of the catheter 20 into a body to be imaged, after which in 123 a sequence of images is captured of the internals of the body, which sequence of images shows an imaged object or anomaly, e.g. an anatomical anomaly such as a coronary stenosis in case of the imaging system 10 being an IVUS imaging system. Although such a sequence of images is typically captured at a known capture rate, e.g. a known frame rate, it is nevertheless difficult to directly determine the size of the anomaly from the sequence of images due to the fact that neighboring images in this sequence typically are non-overlapping, e.g. when capturing 2D slices perpendicular to the translation direction of the catheter 20, with the spacing between subsequent 2D slices being unknown if the translation speed of the catheter 20 is unknown. Therefore, for the size of the anomaly to be accurately determined, the spacing between neighboring images has to be determined to be able to determine the rate of progress of the catheter 20 (e.g. the pullback speed of the catheter 20), which often is unfeasible due to the lack of overlap (i.e. shared anatomical landmarks) in these images.

In 125, the captured images may be processed, e.g. on the patient interface module 30, which processing may include the determination of a first anomaly boundary at point in time $T=T_a$ in 127 and the determination of a second anomaly boundary at point in time $T=T_b$ in 129, with the size of the anomaly typically being defined by the distance between the first anomaly boundary and the second anomaly boundary. However, as explained above, based on this sequence of images alone it is difficult to determine the size of the anomaly due to the unknown spacing between subsequent images in the sequence. Therefore, in accordance with embodiments of the present invention, the size of the anomaly is estimated based on the translation speed S of the catheter 20 as determined in accordance with the method as per the flowchart of FIG. 4. Specifically, in 131, the size of the anomaly SA may be determined by the formula SA=S*$(T_b-T_a)$, i.e. by multiplication of the determined catheter translation speed S with the time delay between the image in which the first anomaly boundary and the image in which the second anomaly boundary is captured. In 131, an indication of the size of the anomaly SA may be generated, e.g. a display control signal for controlling the display device 33 to display the calculated anomaly size.

In this manner, the size of a repair object for repairing the anomaly within the body can be directly determined because the translation speed of the catheter 20 can be accurately determined without requiring well-controlled translation, e.g. pullback, of the catheter 20, i.e. motorized pull-back.

It should be understood that the principles of the present invention may be employed in any suitable type of imaging system including medical imaging systems and non-medical imaging systems. As such systems are well-known per se, a further description of such systems should not be necessary. Nevertheless, an example embodiment of an ultrasound diagnostic imaging system 10 which may employ embodiments of the present invention is described in further detail with the aid of FIG. 6, which schematically depicts a non-limiting example embodiment of such a system.

Figure 6:
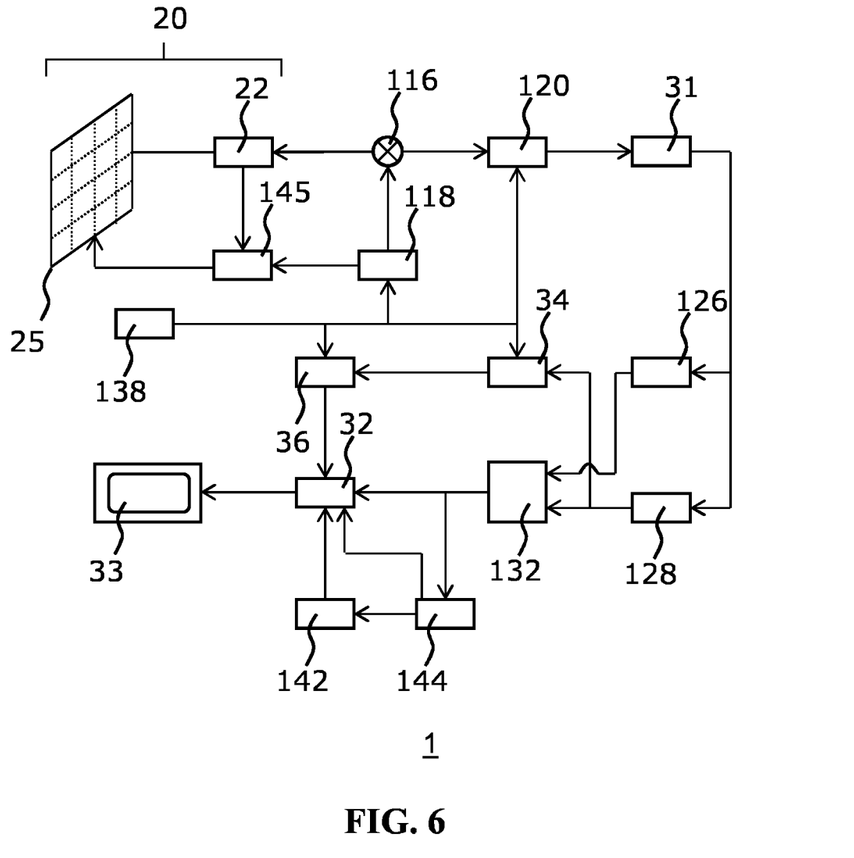
FIG. 6 schematically depicts an example embodiment of an imaging system in more detail.

In FIG. 6, an ultrasonic diagnostic imaging system 10 with a catheter 20 according to an example embodiment of the present invention is shown in block diagram form. In FIG. 6 a transducer array 25 is provided in a catheter 20 for transmitting ultrasonic waves and receiving echo information. The transducer array 25 may be a one- or a two-dimensional array of transducer elements capable of scanning in a 2D plane or in three dimensions for 3D imaging. In some embodiments, the transducer array 25 is a CMUT transducer array although other types of transducer arrays may also be contemplated. The transducer array 25 is coupled to a microbeam former 22 in the catheter 20 which controls transmission and reception of signals by the array cells. Microbeam formers are capable of at least partial beam forming of the signals received by groups or "patches" of transducer elements for instance as described in U.S. Pat. No. 5,997,479 (Savord et al.), U.S. Pat. No. 6,013,032 (Savord), and U.S. Pat. No. 6,623,432 (Powers et al.)

The microbeam former 22 is coupled by the probe cable 27, e.g. coaxial wire, to a transmit/receive (T/R) switch 116 which switches between transmission and reception modes and protects the main beam former 120 from high energy transmit signals when a microbeam former is not present or used and the transducer array 25 is operated directly by the main system beam former 120. The transmission of ultrasonic beams from the transducer array 25 under control of the microbeam former 22 is directed by a transducer controller 118 coupled to the microbeam former by the T/R switch 116 and the main system beam former 120, which receives input from the user's operation of the user interface or control panel 138. One of the functions controlled by the transducer controller 118 is the direction in which beams are steered and focused. Beams may be steered straight ahead from (orthogonal to) the transducer array 25, or at different angles for a wider field of view. The transducer controller 118 may be coupled to control a voltage source 145 for the array 25. For instance, the voltage source 45 sets the DC and AC bias voltage(s) that are applied to the cells of the array 25.

The partially beam-formed signals produced by the microbeam former 12 are forwarded to the main beam former 120 where partially beam-formed signals from individual patches of transducer elements are combined into a fully beam-formed signal. For example, the main beam former 120 may have 128 channels, each of which receives a partially beam-formed signal from a patch of dozens or hundreds of transducer cells of the array 25. In this way the signals received by thousands of transducer elements of a transducer array 25 can contribute efficiently to a single beam-formed signal.

The beam-formed signals are coupled to a signal processor 31. The signal processor 31 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and microbubbles.

The signal processor 31 optionally may perform additional signal enhancement such as speckle reduction, signal compounding, and noise elimination. The bandpass filter in the signal processor 31 may be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals are coupled to a B-mode processor 126 and optionally to a Doppler processor 128. The B-mode processor 126 employs detection of an amplitude of the received ultrasound signal for the imaging of structures in the body such as the tissue of organs and vessels in the body. B-mode images of structure of the body may be formed in either the harmonic image mode or the fundamental image mode or a combination of both for instance as described in U.S. Pat. No. 6,283,919 (Roundhill et al.) and U.S. Pat. No. 6,458,083 (Jago et al.)

The Doppler processor 128, if present, processes temporally distinct signals from tissue movement and blood flow for the detection of the motion of substances, such as the flow of blood cells in the image field. The Doppler processor typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material.

This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor receives and processes a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue. The structural and motion signals produced by the B-mode (and Doppler) processor(s) are coupled to a scan converter 132 and a multiplanar reformatter 144. The scan converter 132 arranges the echo signals in the spatial relationship from which they were received in a desired image format. For instance, the scan converter may arrange the echo signal into a two dimensional (2D) sector-shaped format, or a pyramidal three dimensional (3D) image.

The scan converter can overlay a B-mode structural image with colors corresponding to motion at points in the image field with their Doppler-estimated velocities to produce a color Doppler image which depicts the motion of tissue and blood flow in the image field. The multiplanar reformatter 144 will convert echoes which are received from points in a common plane in a volumetric region of the body into an ultrasonic image of that plane, for instance as described in U.S. Pat. No. 6,443,896 (Detmer). A volume renderer 142 converts the echo signals of a 3D data set into a projected 3D image as viewed from a given reference point as described in U.S. Pat. No. 6,530,885 (Entrekin et al.).

The 2D or 3D images are coupled from the scan converter 132, multiplanar reformatter 144, and volume renderer 142 to an image processor 32 for further enhancement, buffering and temporary storage for display on an image display 40. In addition to being used for imaging, the blood flow values produced by the Doppler processor 128 and tissue structure information produced by the B-mode processor 126 are coupled to a quantification processor 34. The quantification processor produces measures of different flow conditions such as the volume rate of blood flow as well as structural measurements such as the sizes of organs and gestational age. The quantification processor may receive input from the user control panel 138, such as the point in the anatomy of an image where a measurement is to be made.

Output data from the quantification processor is coupled to a graphics processor 36 for the reproduction of measurement graphics and values with the image on the display 33. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 138, such as patient name.

The user interface is also coupled to the transmit controller 118 to control the generation of ultrasound signals from the transducer array 25 and hence the images produced by the transducer array and the ultrasound system. The user interface is also coupled to the multiplanar reformatter 144 for selection and control of the planes of multiple multiplanar reformatted (MPR) images which may be used to perform quantified measures in the image field of the MPR images.

As will be understood by the skilled person, the above embodiment of an ultrasonic diagnostic imaging system is intended to give a non-limiting example of such an ultrasonic diagnostic imaging system. The skilled person will immediately realize that several variations in the architecture of the ultrasonic diagnostic imaging system are feasible without departing from the teachings of the present invention. For instance, as also indicated in the above embodiment, the microbeam former 22 and/or the Doppler processor 128 may be omitted, the catheter 20 may not have 3D imaging capabilities and so on. Other variations will be apparent to the skilled person.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An imaging system comprising:
   a catheter;
   an imaging arrangement on the catheter for generating an image with the catheter; a sensor arrangement comprising a first sensor at a first location on the catheter and a second sensor at a second location on the catheter, the first location and second location being at a set distance (D) from each other; and
   a processing arrangement communicatively coupled to the sensor arrangement and adapted to:
   process a first sensor signal provided by the first sensor indicative of the first sensor in a reference location (X) at a first point in time;
   process a second sensor signal provided by the second sensor indicative of the second sensor in the reference location at a second point in time; and
   determine a translation speed (S) of the catheter from the set distance and the difference between the first point in time and the second point in time;
   wherein the processing arrangement is adapted to identify the reference location by matching the processed first sensor signal to the processed second sensor signal; and
   wherein either:
   the first sensor and the second sensor are respective first and second ultrasound transducer arrays,
   the imaging arrangement comprises the first sensor and/or the second sensor, and
   the processing arrangement is adapted to identify the reference location by matching a first ultrasound image generated from the first sensor signal to a second ultrasound image generated from the second sensor signal;
   or:
   the first sensor and the second sensor are respective first and second pressure sensors,
   the imaging arrangement comprises an ultrasound transducer array, and
   the processing arrangement is adapted to identify the reference location by matching a pressure profile obtained from the processed first sensor signal to a pressure profile obtained from the processed second sensor signal.

2. The imaging system of claim 1, wherein the processing arrangement is further adapted to:
   determine a size of an anatomical anomaly imaged with the imaging arrangement based on the determined translation speed of the catheter; and
   generate an output indicative of the determined size of said anatomical anomaly.

3. The imaging system of claim 1, wherein the at least one sensor on the catheter is configured for generating an in-vivo ultrasound image.

4. The imaging system of claim 1, wherein:
   the first sensor is arranged to generate a first plurality of temporally discrete first sensor signals;
   the second sensor is arranged to generate a second plurality of temporally discrete second sensor signals; and
   the processor arrangement is arranged to select, based on a previously determined translation speed of the catheter:
   a second sensor signal from said second plurality for matching to a first sensor signal from said first plurality; or
   a first sensor signal from said first plurality for matching to a second sensor signal from said second plurality.

5. The imaging system of claim 1 when the first sensor and the second sensor are respective first and second ultrasound transducer arrays, wherein the processing arrangement is adapted to match the first ultrasound image to the second ultrasound image by identification of a same image feature in the first ultrasound image and the second ultrasound image.

6. The imaging system of claim 5, wherein the processing arrangement is adapted to match the first ultrasound image to the second ultrasound image by:
   calculating a correlation (C) between the first ultrasound image and the second ultrasound image; and
   determining that the first ultrasound image matches the second ultrasound image if the calculated correlation exceeds a threshold value.

7. The imaging system of claim 5, wherein the processing arrangement is further adapted to perform at least one image adjustment operation on at least one of the first ultrasound image and the second ultrasound image prior to matching the first ultrasound image to the second ultrasound image.

8. A method of determining a translation speed (S) of a translatable tool of a medical imaging system, the medical imaging system further comprising an imaging arrangement including at least one sensor on the tool for generating an image with the tool a sensor arrangement comprising a first sensor at a first location on the tool and a second sensor at a second location on the tool, the first location and second location being at a set distance (D) from each other, the method comprising:
   processing a first sensor signal provided by the first sensor indicative of the first sensor in a reference location at a first point in time;
   processing a second sensor signal provided by the second sensor indicative of the second sensor in the reference location at a second point in time; and
   determining the translation speed of the tool from the set distance and the difference between the first point in time and the second point in time wherein the method further comprises identifying the reference location by matching the processed first sensor signal to the processed second sensor signal; and
   wherein either:
   the first sensor and the second sensor are respective first and second ultrasound transducer arrays, and the imaging arrangement comprises the first sensor and/or the second sensor, so that the identifying of the reference location is by matching a first ultrasound image generated from the first sensor signal to a second ultrasound image generated from the second sensor signal;
   or:
   the first sensor and the second sensor are respective first and second pressure sensors, and the at least one sensor on the tool for generating an image with the tool comprises an ultrasound transducer array, so that the identifying of the reference location is by matching a pressure profile obtained from the processed first sensor signal to a pressure profile obtained from the processed second sensor signal.

9. The method of claim 8, further comprising:
   generating a sequence of images indicative of a size of an imaged object with the imaging arrangement over a period of time;
   calculating the size of the imaged object from the period of time and the determined translation speed of the tool; and generating an indication of the calculated size of the imaged object.

10. The method of claim 8, wherein the reference point is an image feature.

11. The method of claim 9 when the first sensor and the second sensor are respective first and second ultrasound transducer arrays, wherein matching the first ultrasound image to the second ultrasound image comprises identifying the same image feature in the first ultrasound image and the second ultrasound image.

12. The method of claim 11, wherein matching the first ultrasound image to the second ultrasound image comprises:
calculating a correlation (C) between the first ultrasound image and the second ultrasound image; and
determining that the first ultrasound image matches the second ultrasound image if the calculated correlation exceeds a threshold value.

13. The method of claim 11, further comprising:
performing at least one image adjustment operation on at least one of the first ultrasound image and the second ultrasound image prior to matching the first ultrasound image to the second ultrasound image.

14. A medical imaging interventional tool comprising:
an imaging arrangement communicatively connectable to a processing arrangement and comprising at least one sensor on the tool for generating an image; a sensor arrangement comprising a first sensor at a first location on the tool and a second sensor at a second location on the tool, the first location and second location being at a set distance (D) from each other,
wherein, when the interventional tool is being translated with a translation speed (S), the first sensor is arranged to provide the processing arrangement with a first sensor signal indicative of the first sensor in a reference location (X) at a first point in time and the second sensor is arranged to provide the processing arrangement with a second sensor signal indicative of the second sensor in the reference location at a second point in time, so that the processing arrangement can determine the translation speed (S) of the interventional tool from the set distance and the difference between the first point in time and the second point in time by matching the processed first sensor signal to the processed second sensor signal to identify the reference location; and
wherein either the first sensor and the second sensor are respective first and second ultrasound transducer arrays, and the imaging arrangement comprises the first sensor and/or the second sensor;
or the first sensor and the second sensor are respective first and second pressure sensors, and the at least one sensor on the tool for generating an image comprises an ultrasound transducer array.

15. A processing arrangement for determining a translation speed (S) of a medical imaging interventional tool of claim 14, the processing arrangement being communicatively connectable to the sensor arrangement of the medical imaging interventional tool and adapted to:
process a first sensor signal provided by the first sensor of the sensor arrangement of the tool and indicative of the first sensor in a reference location (X) at a first point in time;
process a second sensor signal provided by the second sensor of the sensor arrangement of the medical imaging interventional tool and indicative of the second sensor in the reference location at a second point in time; and
determine the translation speed (S) of the tool from the set distance and the difference between the first point in time and the second point in time;
wherein the processing arrangement is adapted to identify the reference location by matching the processed first sensor signal to the processed second sensor signal; and
wherein the processing arrangement is adapted to identify the reference location by either:
matching a first ultrasound image generated from the first sensor signal to a second ultrasound image generated from the second sensor signal, if the first sensor and the second sensor are respective first and second ultrasound transducer arrays;
or:
matching a pressure profile obtained from the processed first sensor signal to a pressure profile obtained from the processed second sensor signal, if the first sensor and the second sensor are respective first and second pressure sensors.

* * * * *